(12) United States Patent
Sang et al.

(10) Patent No.: US 9,831,061 B2
(45) Date of Patent: Nov. 28, 2017

(54) METHODS, SYSTEMS, AND COMPUTER READABLE MEDIA FOR MEASURING AND CORRECTING DRIFT DISTORTION IN IMAGES OBTAINED USING A SCANNING MICROSCOPE

(71) Applicant: North Carolina State University, Raleigh, NC (US)

(72) Inventors: Xiahan Sang, Raleigh, NC (US); James Michael LeBeau, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/103,154

(22) PCT Filed: Dec. 9, 2014

(86) PCT No.: PCT/US2014/069405
§ 371 (c)(1),
(2) Date: Jun. 9, 2016

(87) PCT Pub. No.: WO2015/089113
PCT Pub. Date: Jun. 18, 2015

(65) Prior Publication Data
US 2016/0322191 A1    Nov. 3, 2016

Related U.S. Application Data

(60) Provisional application No. 61/913,884, filed on Dec. 9, 2013.

(51) Int. Cl.
*G01N 23/00* (2006.01)
*H01J 37/22* (2006.01)
(Continued)

(52) U.S. Cl.
CPC ............ *H01J 37/222* (2013.01); *G01N 23/04* (2013.01); *G01N 23/2251* (2013.01);
(Continued)

(58) Field of Classification Search
CPC .. H01J 37/00; H01J 37/02; H01J 37/22; H01J 37/222
(Continued)

(56) References Cited

U.S. PATENT DOCUMENTS 5,412,764 A    5/1995 Tanaka
5,901,241 A    5/1999 Koljonen et al.
(Continued)

FOREIGN PATENT DOCUMENTS

EP    2 584 362 A1    4/2013

OTHER PUBLICATIONS

Notification of Transmittal of the International Search Report and the Written Opinion of the International Searching Authority, or the Declaration for PCT International Application No. PCT/US2014/069405 (dated Mar. 4, 2015).
(Continued)

*Primary Examiner* — Jason McCormack
(74) *Attorney, Agent, or Firm* — Jenkins, Wilson, Taylor & Hunt, P.A.

(57) ABSTRACT

The subject matter described herein includes methods, systems, and computer readable media for measuring and correcting drift distortion in images obtained using the scanning microscope. One method includes obtaining an image series of a sample acquired using scanning-microscope by rotating scan coordinates of the microscope between successive image frames. The method further includes determining at least one measurement of an angle or a distance associated with an image feature as a function of rotation angle from the series of rotated images. The
(Continued)

method further includes using the at least one measurement to determine a model for drift distortion in the series of images. The method further includes using the drift distortion model to generate a drift corrected image from the series of images.

21 Claims, 11 Drawing Sheets

(51) Int. Cl.
  *G01N 23/225* (2006.01)
  *G01N 23/04* (2006.01)
  *H01J 37/28* (2006.01)
(52) U.S. Cl.
  CPC ........ *H01J 37/28* (2013.01); *G01N 2223/401* (2013.01); *G01N 2223/418* (2013.01); *H01J 2237/2802* (2013.01)
(58) Field of Classification Search
  USPC .............................. 250/306, 307, 310, 311
  See application file for complete search history.

(56) References Cited

U.S. PATENT DOCUMENTS

| | | |
|---|---|---|
| 6,252,926 B1 | 6/2001 | Flohr et al. |
| 2003/0128895 A1 | 7/2003 | Schweid |
| 2004/0131241 A1 | 7/2004 | Curry et al. |
| 2006/0219908 A1 | 10/2006 | Inada et al. |
| 2009/0127474 A1* | 5/2009 | Tsuneta .................. H01J 37/20 250/442.11 |
| 2011/0073757 A1 | 3/2011 | Tanaka |
| 2011/0240854 A1 | 10/2011 | Terada et al. |
| 2012/0127320 A1 | 5/2012 | Balogh |
| 2012/0287258 A1 | 11/2012 | Tsuneta et al. |
| 2013/0254948 A1 | 9/2013 | Hartong et al. |

OTHER PUBLICATIONS

Snella, "Drift Correction for Scanning-Electron Microscopy," Submitted to the Department of Electrical Engineering and Computer Science at MIT—Masters Thesis, pp. 1-92 (Sep. 2010).
Zuo et al., "Lattice and strain analysis of atomic resolution Z-contrast images based on template matching," Ultramicroscopy, 136, p. 50-60 (2014).
Aso et al., "Atomic level observation of octahedral distortons at the perovskite oxide heterointerface," Sci. Rep., 3, p. 1-6 (2013).
Jones et al., "Identifying and Correcting Scan Noise and Drift in the Scanning Transmission Electron Microscope," Microsc, Mlcroanal., 19, p. 1050-1060 (2013).
Follin et al., "Three-axis correction of distortion due to positional drift in scanning probe microscopy," AIP Review of Scientific Instruments, 83, p. 083711-1-083711-7 (2012).
Berkels et al., "High Precision STEM Imaging by Non-Rigid Alignment and Averaging of a Series of Short Exposures," Microsc. Microanal., 18, p. 300-301 (2012).
Binev et al., High Quality Image Formation by Nonlocal Means Applied to High-Angle Annular Darkfield Scanning Transmission Electron Microscopy (HAADF-STEM), Institut fur Geometrie und Praktische Mathematik, Aachen, Germany p. 1-21 (Dec. 2010).

Braidy et al., "Correcting scanning instabilities from images of periodic structures," Ultramicroscopy, 118, p. 67-76 (2012).
Klein et al., "Multimodal image registration by edge attraction and regularization using a B-spline grid," SPIE, Lake Buena Vista, Florida, USA p. 1-8 (2011).
Nelson et al., "Spontaneous Vortex Nanodomain Array at Ferroelectric Heterointerfaces," Nano Letters, 11, p. 828-834 (2011).
Borisevich et al., "Mapping Octahedral Tilts and Polarization Across a Domain Wall in BiFe03 from Z-Contrast Scanning Transmission Electron Microscopy Image Atomic Column Shape Analysis," ACS Nano, 4, p. 6071-6079 (2010).
Borisevich et al., "Suppression of Octahedral Tilts and Associated Changes in Electronic Properties at Epitaxial Oxide Hetrostructure Interfaces," Phys. Rev. Lett., 105, p. 087204-1-087204-4 (2010).
Buban et al., "High-resolution low-dose scanning transmission electron microscopy," Journal of Electron Microscopy, 59, p. 103-112 (2010).
Kimoto et al., "Local crystal structure analysis with several picometer precision using scanning transmission electron microscopy," Ultramicroscopy, 110, p. 778-782 (2010).
Salmons et al., "Correction of distortion due to thermal drift in scanning probe microscopy," Ultramicroscopy, vol. 110, Issue 4, p. 339-349 (2010).
Pennycook et al., "Aberration-corrected scanning transmission electron microscopy: from atomic imaging and analysis to solving energy problems," Philosophical Transactions of the Royal Society A: Mathematical, Physical and Engineering Sciences, 367, p. 3709-3733 (2009).
Saito et al., "Local crystal structure analysis with 10-pm accuracy using scanning transmission electron microscopy," Journal of Electron Microscopy 58, p. 131-136 (2009).
Krivanek et al., "An electron microscope for the aberration-corrected era," Ultramicroscopy 108, ScienceDirect p. 179-195 (2008).
Klie et al., "Atomic-Resolution STEM in the Aberration-Corrected JEOL JEM2200FS," Microsc, Microanal., 14, p. 104-112 (2008).
LeBeau et al., "Quantitative Atomic Resolution Scanning Transmission Electron Microscopy," Phys. Rev, Lett., 100, p. 206101-1-206101-4 (2008).
Gipson et al., "2dx—User-friendly image processing for 2D crystals," J Struct Biol, 157, p. 64-72 (2007).
Muller et al., "Room design for high-performance electron microscopy," Ultramicroscopy, 106, p. 1033-1040 (2006).
Hue et al., "Calibration of projector lens distortions," Journal of Electron Microscopy, 54, p. 181-190 (2005).
Recnik et al., "IMAGE-WARP: A real-space restoration method for high-resolution STEM images using quantitative HRTEM analysis," Ultramicroscopy, 103, p. 285-301 (2005).
Muller et al., "Optimizing the environment for sub-0.2 nm scanning transmission electron microscopy," Journam of Electron Microscopy, 50, pg. 297-226 (2001).
Hytch et al., "Quantitative measurement of displacement and strain fields from HREM micrographs," Ultramicroscopy, 74, p. 131-146 (1998).
Lagarias et al., "Convergence Properties of the Nelder-Mead Simplex Method in Low Dimensions," SIAM Journal of Optimization, 9, p. 112-147 (1998).
Nellist et al., "Accurate structure determination from image reconstruction in ADF STEM," J. Microsc., 190, p. 159-170 (1998).
Harrach, "Instrumental factors in high-resolution FEG STEM," Ultramicroscopy, 58, p. 1-5 (1995).

* cited by examiner

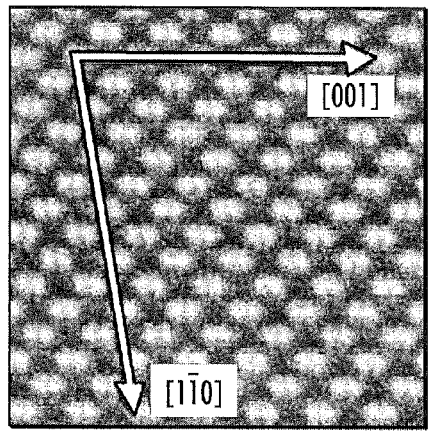
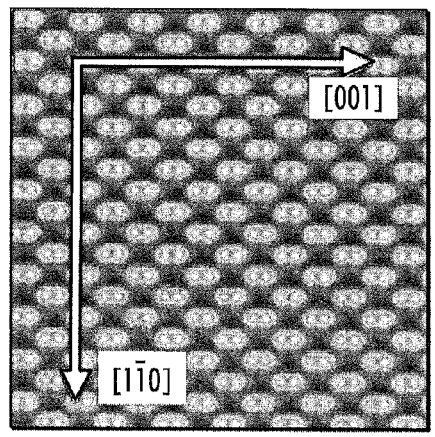
FIG. 7A　　　　　　　　　　FIG. 7B
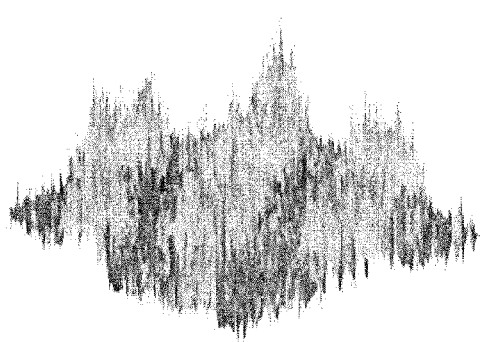
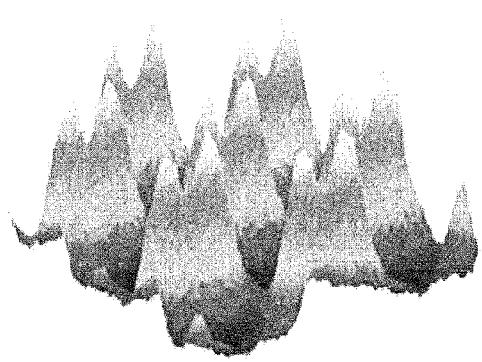
FIG. 7C　　　　　　　　　　FIG. 7D

METHODS, SYSTEMS, AND COMPUTER READABLE MEDIA FOR MEASURING AND CORRECTING DRIFT DISTORTION IN IMAGES OBTAINED USING A SCANNING MICROSCOPE

PRIORITY CLAIM

This application claims the benefit of U.S. Provisional Patent Application Ser. No. 61/913,884, filed Dec. 9, 2013; the disclosure of which is incorporated herein by reference in its entirety.

TECHNICAL FIELD

The subject matter described herein relates to correcting distortion in images obtained with a scanning microscope. More particularly, the subject matter described herein relates to methods, systems, and computer readable media for measuring and correcting drift distortion in images obtained using a scanning microscope.

BACKGROUND

In scanning microscopy, such as scanning transmission electron microscopy (STEM), scanning electron microscopy (SEM), or scanning probe microscopy (SPM), it is desirable to image samples consistently and with minimal image distortion. One type of distortion that occurs in scanning microscopy imaging is drift distortion. For example, thermal expansion of a sample holder, vibration, air flow, and electromagnetic fields may cause the sample to move in one or more directions while being scanned by the beam of the microscope. This movement causes distortion along one or more directions in the image. This distortion caused by sample movement during scanning is referred to as drift distortion. Drift distortion corrupts image features and can be difficult to quantify.

One possible solution to the problem of drift distortion is to correct the distortion in the final image using a-priori knowledge of the sample structure. For example, if the structure of the sample is known, distorted images can be corrected based on the known structure. However, a-priori knowledge of structural information of the sample is not always available. Accordingly, it is desirable to measure and correct drift distortion without requiring advance knowledge of sample structure.

Another method for reducing drift distortion is to wait for thermal stability of the sample holder before acquiring sample images. Such waiting reduces drift distortion caused by thermal inequilibrium of the sample and/or the sample holder with the microscope. However, waiting for thermal equilibrium before acquiring each image greatly increases the time required to obtain a series of scanned microscopy images and is undesirable for high throughput analysis.

Yet another method for reducing or correcting for drift distortion is to rapidly obtain multiple short exposure time images and average the images. While such averaging can reduce drift distortion, the final average image can still contain drift distortion, especially for large image frame sizes.

Accordingly, in light of these difficulties, there exists a need for improved methods, systems, and computer readable media for measuring and correcting drift distortion in a scanning microscopy system.

SUMMARY

The subject matter described herein includes revolving scanning transmission electron microscopy—RevSTEM—a technique that enables the characterization and removal of sample drift distortion from STEM images without the need for a-priori crystal structure information. To measure and correct for drift distortion, we acquire an image series while rotating the scan coordinate system between successive frames. Through theory and experiment, we show that the revolving image series captures the information necessary to analyze sample drift rate and direction. At atomic resolution, we quantify the image distortion using the projective standard deviation, a rapid, real-space method to directly measure lattice vector angles. By fitting these angles to a physical model, we show that the refined drift parameters provide the input needed to correct distortion across the series. We demonstrate that RevSTEM simultaneously enables routine picometer precision and accuracy, leads to a dramatically improved signal-to-noise ratio, and removes the need for a-priori sample structure information regardless of drift rate.

The subject matter described herein includes methods, systems, and computer readable media for measuring and correcting drift distortion in images obtained using the scanning microscope. One method includes obtaining an image series acquired using scanning microscope by rotating scan coordinates of the microscope between successive image frames. The method further includes determining at least one measurement of an angle or distance associated with an image feature as a function of rotation angle from the series of rotated images. The method further includes using the at least one measurement to determine a model for drift distortion in the series of images. The method further includes using drift distortion model to generate a drift corrected image from the series of images.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 7A is an image of the first frame of the Si ⟨110⟩ RevSTEM image series. FIG. 7B is the final RevSTEM image after distortion correction and averaging. FIGS. 7C and 7D are three dimensional surface plots of the first acquired frame and the final image respectively.

DETAILED DESCRIPTION

1. Introduction

While scanning transmission electron microscopy (STEM) has proven essential to the atomic scale characterization of materials, measurement of atomic displacements and distances is hampered by the presence of sample drift, e.g. at defects, interfaces, or even in perfect crystals [4-6, 16]. Sample drift during image acquisition introduces distortion proportional to the drift rate, preventing the accurate measurement of atomic structure. Though modern STEM installations are optimized to reduce vibration, air flow/fields, and temperature fluctuations, some sample drift is typically still present [14, 15].

Various methods have been applied to limit the effects of sample drift. When the drift rate is constant, the resulting image distortion can be assumed uniform. In this case, a defect-free region with known crystal structure can serve as a reference. This reference area can then be matched to the known structure by an affine transformation [18]. Alternatively, Rečnik et al. demonstrated that information from parallel imaging (conventional high resolution TEM) can be used to register the STEM image and correct for the distortion [21]. This method, however, requires finding the same area or defect in both imaging modes. Another approach uses an image series with each frame acquired using a short probe dwell time at each pixel [8]. These images can then be aligned by cross-correlation and averaged together [11,12]. Recently, Berkels et al., for example, achieved measurement precision of 0.7 pm by a non-rigid frame averaging method applied to a series of 256×256 pixel images acquired with short 0.8 s exposures [22, 23]. While small images can be used to effectively eliminate drift, the available area for structural analysis is minimized by the large spatial sampling rate. Unless the sample is very stable during acquisition, large frames will contain distortion that is then transferred into the final average.

Figure 1A:
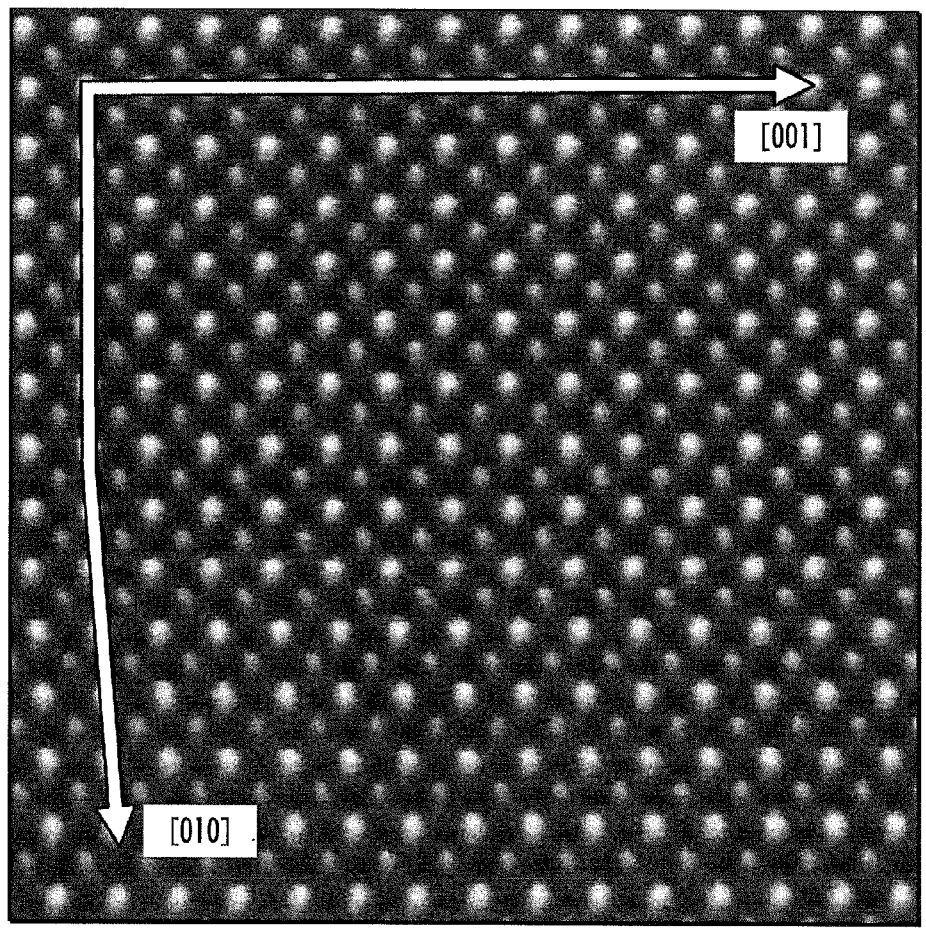
FIG. 1A illustrates an HAADF STEM image of [001] oriented $SrTiO_3$ exhibiting image distortion due to drift. Note that the apparent [010] direction changes across the image due to drift.
Figure 1B:
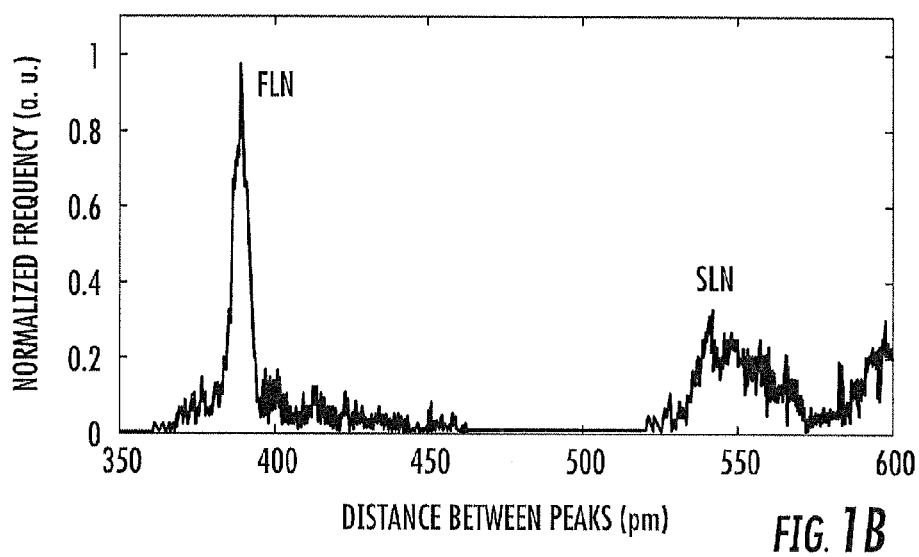
FIG. 1B illustrates FLN and SLN distance histogram calculated from peak locations determined by fitting atom column intensities to a Gaussian distribution [22].

Specimen drift during an acquisition can cause expansion, compression, and/or shearing of the image. As a typical example, FIG. 1A shows a high angle annular dark-field (HAADF) STEM image of [100] $SrTiO_3$ acquired with a 20 μs dwell time and frame size of 1024×1024 pixels. While the [001] and [010] directions should be perpendicular, the observed angle between them is approximately 85° and changes across the image. By measuring the distance between the first like neighbors (FLN), i.e. Sr-Sr and Ti-Ti, we find a major peak at the lattice parameter distance (a=390.5 pm), but with significant variation and standard deviation, σ=2.6 pm. The problem is compounded for the second like neighbor (SLN) distance ($\sqrt{2}$a): only a diffuse peak is found with σ=10.3 pm. The peak broadening is due to a combination of drift distortion, scan noise, and the low signal to noise ratio (SNR) available in a single image acquisition [18]. Furthermore, the angle of the [010] direction varies across the image. These features indicate that drift has severely limited the available crystallographic information.

In the present work, we introduce revolving scanning transmission electron microscopy (RevSTEM). The method uses a series of fast-acquisition STEM images, but with the scan coordinates rotated between successive frames. This scan rotation introduces a concomitant change in image distortion that we use to analyze the sample drift rate and direction. We provide a theoretical basis for the approach and introduce the projective standard deviation (PSD) to quantify lattice vector angles in atomic resolution images. By measuring the lattice vector angles across the rotation series, we fit the observed angular distortions to a physical drift model. The resulting drift parameters are then used to calculate an inverse affine transformation matrix needed to restore each image. For a demonstration of the technique, we provide two case studies. We first apply the technique to STEM images of (110) Si acquired while the sample was experiencing a measured drift rate of 530 pm/s. Second, we apply RevSTEM imaging to (100) $SrTiO_3$ to evaluate the accuracy and precision that can be achieved with this technique. In both cases, we demonstrate that RevSTEM achieves near perfect restoration of the image series with <0.3% error and is independent of frame size.

2. Experiment

In one experiment for illustrating the effectiveness of RevSTEM, SrTiO$_3$ and Si samples were prepared by wedge polishing and subsequent ion-milling to electron transparency using a Fischione 1010 ion mill. The STEM images were acquired, using a probe corrected FEI Titan G2 60-300 kV S/TEM equipped with an X-FEG source operated at 200 kV. The convergence and collection inner semi-angles were 21 mrad and 77 mrad respectively. The probe intensity was 80-100 pA. TEM imaging and analysis (TIA) and FEI Tecnai scripting were used to acquire the RevSTEM image series. Scan distortion was corrected using the built-in FEI program with a standard SPI cross-grating replica with a spacing of 2160 lines per mm. After correction of the scan coil distortion, the angular distortion was generally within 0.1° at low magnifications.

For the <110> Si HAADF RevSTEM dataset, 60 images were acquired while the sample was experiencing significant drift. Each 1024×1024 frame was acquired with a dwell time of 3 µs/pixel. The frame time was thus approximately 3 s for a total acquisition time of 180 s. The scan coordinates were rotated 6° clockwise after each frame was acquired, equivalent to a 6° counter-clockwise rotation of the image. We note that no attempt was made to keep the same sample region within the imaging area, i.e. no active drift correction was applied. For SrTiO$_3$, a HAADF RevSTEM series was acquired along the [100] zone axis. The dwell time for each pixel was 5 µs with an image dimension of 512×512 pixels. The scan coordinates were rotated 90° clockwise after each frame acquisition. (3)

3. Mathematical Description of RevSTEM

Let us begin by considering the distortions introduced by specimen drift during STEM image acquisition. For a constant drift rate, d, the result is to distort the image through a dilatation, contraction, and/or shearing. The distortion will also depend on the size of the scan area, defined as $l_x \times l_y$, and the time required to scan the whole frame, $\tau$. The distortion of the ideal image due to drift is shown schematically in FIG. 2. The slow (vertical) and fast (horizontal) scan directions are defined as $\vec{X}$ and $\vec{Y}$ respectively. While the STEM image dimensions are fixed by $l_x \times l_y$, (unshaded area bounded by a square in FIG. 2), the actual scanned sample area (shaded area in FIG. 2) is a distorted parallelogram due to drift. Here, this distortion is modeled as an affine transformation described by a matrix [T] that transforms $\vec{v}_0$ to $\vec{v}_d$ as in FIG. 2 and satisfies [26]:

$$[T] \times (\vec{v}_y, \vec{v}_0) = (\vec{v}_y, \vec{v}_d) \quad (1)$$

Figure 2:
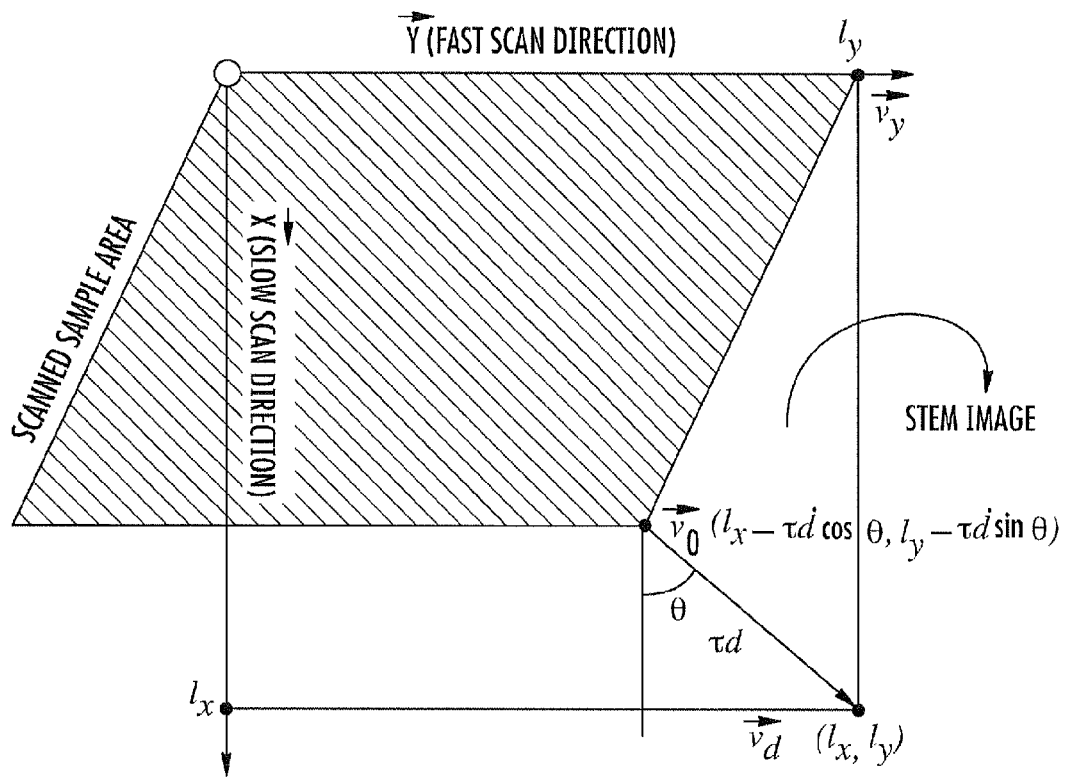
FIG. 2 is a schematic diagram showing the distortion introduced during STEM imaging of a sample experiencing drift. The actual scanned sample area is represented by the parallelogram (shaded) and the actual image by the square (unshaded).

Note that [T] leaves the first scan line of the image, $\vec{v}_y$, unchanged as it represents an insignificant fraction of the total frame time $\tau$ and thus contributes negligible distortion. In equation 1, $\vec{v}_y = (0, l_y)'$ and $\vec{v}_y = (l_x, l_y)'$, where ' indicates the transpose. The magnitude of the vector that connects $\vec{v}_0$ to $\vec{v}_d$ is given by $\tau \dot{d}$. In FIG. 2, the drift angle relative to the slow scan direction is $\theta$, yielding $\vec{v}_0 = (l_x - \tau \dot{d} \cos(\theta), l_y - \tau \dot{d} \sin(\theta))'$. [T] is then the solution of:

$$[T] \times \begin{pmatrix} 0 & l_x - \tau \dot{d} \cos(\theta) \\ l_y & l_y - \tau \dot{d} \sin(\theta) \end{pmatrix} = \begin{pmatrix} 0 & l_x \\ l_y & l_y \end{pmatrix} \quad (2)$$

To solve for [T], we need to determine the drift rate d and the drift angle $\theta$. Without a direct measurement of drift rate and direction, a reference area with known crystal structure is usually used to restore the image. This is particularly limiting if such a reference area is not available in the same image frame. When the crystal structure of the materials is known, Jones and Nellist have demonstrated an approach to correct for STEM image drift distortions using the known lattice vector angles [18].

Figure 3A:
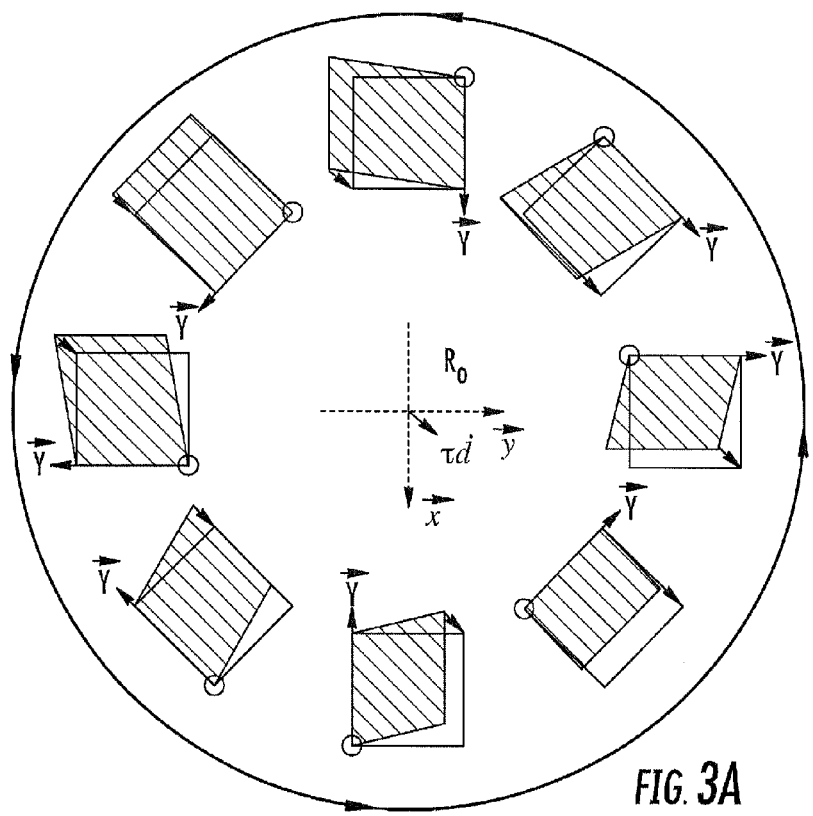
FIG. 3A is a schematic representation of RevSTEM where the encompassing circle represents the image rotation. The sample drift vector is indicated by thick arrows between the shaded and unshaded areas. The sample coordinate system (dashed lines) is provided at the center and surround by the scanned sample area (shaded) and actual image (unshaded) for each rotation. At each rotation, the fast scan direction ($\vec{Y}$) is indicated by a thick arrow and the slow scan direction follows the right hand rule with the origin at the small circles.

Consider instead, an image series acquired with a scan rotation introduced between each frame. As the scan coordinates are rotated by an angle, $\alpha$, relative to the specimen drift direction, the observed image distortion will be concomitantly modified. This is shown schematically in FIG. 3A where the scanned sample area is compared with the STEM image for eight rotation angles ranging from 0° to 315° with a step size of 45°. The fixed sample coordination system, $\mathbb{R}_{00}$, is indicated in FIG. 3A as $\vec{x}$ and $\vec{y}$. At the microscope, a counter-clockwise image rotation, +$\alpha$, corresponds to a clockwise, $-\alpha$, rotation of the scan coordinate system. The rotated coordination system is then referred to as $\mathbb{R}_{0\alpha}$, with the fast (horizontal) scan direction, $\vec{Y}$, indicated by the arrows originating from the origin and pointing towards each $\vec{Y}$. The drift vector (arrows from the shaded to unshaded regions) is then rotated relative to the slow (vertical) scan direction where $\theta$ is modified by an amount $\Delta \alpha$. The drift vector, however, remains fixed relative to $\mathbb{R}_{00}$, as shown in the figure.

Figure 3B:
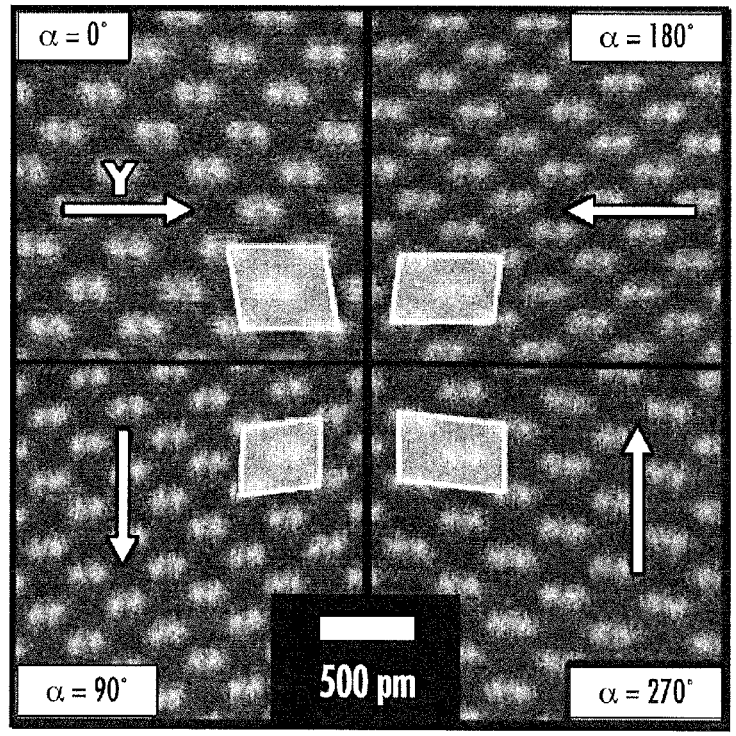
FIG. 3B illustrates select frames from the Si ⟨110⟩ RevSTEM dataset with as indicated in each image. Each frame has been rotated by −α and a unit cell has been highlighted for comparison.

The RevSTEM concept is demonstrated using an experimental Si <110> dataset as shown in FIG. 3B. From the 60 image series, only frames for rotation angles equal to 0°, 90°, 180° and 270° are shown for comparison. As expected from the parallelogram shape of the scanned sample area, the images are distorted opposite to fill the square frame. Furthermore, the distortion in $\alpha=0°$ is opposite to that of $\alpha=180°$ because the drift vector is fixed in $\mathbb{R}_{00}$. Next, we show that recording these distortions as a function of $\alpha$ is essential to derive the drift rate and angle without prior knowledge of the sample.

Based on this schematic description, the transformation matrix must be expanded to account for the scan rotation and a time varying drift rate d(t). This is readily achieved by incorporating $\alpha$ into Eqn. 2 and where $[T_\alpha]$ satisfies:

$$[T_\alpha] \times \begin{pmatrix} 0 & l_x - \tau \dot{d}(t) \cos(\theta + \alpha) \\ l_y & l_y - \tau \dot{d}(t) \sin(\theta + \alpha) \end{pmatrix} = \begin{pmatrix} 0 & l_x \\ l_y & l_y \end{pmatrix} \quad (3)$$

For simplicity we assume that the STEM image is square, i.e. $l_x = l_y$, which is often the case. We also introduce a time dependent, unit-less drift parameter, D(t), defined as $\tau \dot{d}(t)/l_x$. The matrices $[T_\alpha]$ and $[T_\alpha]^{-1}$ are then given by:

$$[T_\alpha] = \begin{pmatrix} \dfrac{1}{1 - D(t)\cos(\theta + \alpha)} & 0 \\ \dfrac{D(t)\sin(\theta + \alpha)}{1 - D(t)\cos(\theta + \alpha)} & 1 \end{pmatrix} \quad (4)$$

and

-continued $$[T_\alpha]^{-1} = \begin{pmatrix} 1 - D(t)\cos(\theta + \alpha) & 0 \\ -D(t)\sin(\theta + \alpha) & 1 \end{pmatrix} \quad (5)$$

$[T_\alpha]^{-1}$ represents affine transformation matrix that restores the experimental STEM images to the actual scanned sample areas. To evaluate the two key parameters, $D(t)$ and $\theta$ a measurement of the image distortion is required across the RevSTEM series. For atomic resolution imaging, the angle between the lattice vectors and a fixed vector in $\mathbb{R}_{0\,0}$, referred to herein as a lattice vector angle ($\beta$), provides an ideal metric: they would remain constant if the sample was perfectly stable without drift.

3.1. Measuring the Lattice Vector Angles

Typically, the angles between lattice planes are determined in reciprocal space using the Fourier transform (FT). There are however, significant limitations to this approach for RevSTEM drift measurement and correction. For STEM images with fast acquisitions times, as with RevSTEM, the low SNR, scan distortions, and aperiodic image boundaries are carried into reciprocal space. These features lead to complicated and imprecise analysis. Further, a sufficiently large number of unit cells is required in the image area, as needed to achieve high sampling in reciprocal space and hence precise angle measurements.

Figure 4A:
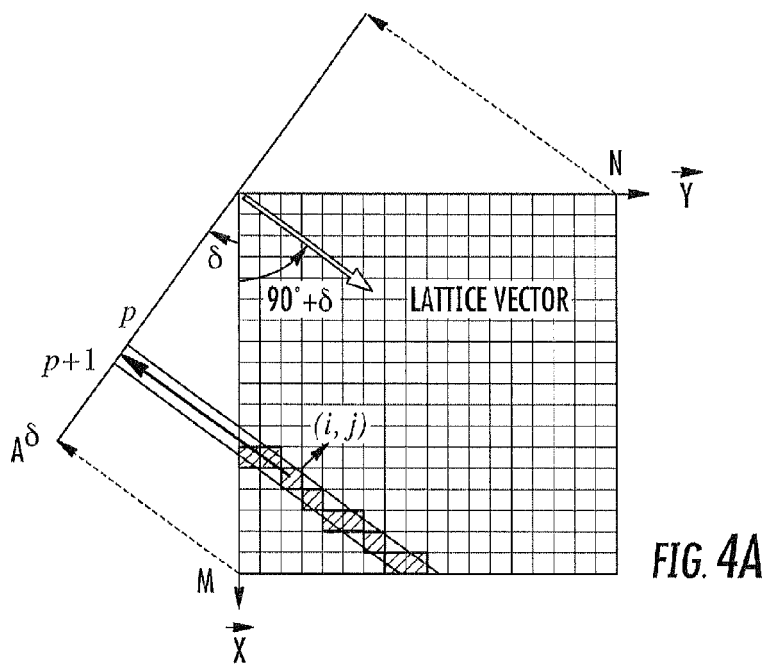
FIG. 4A is a schematic representation of calculating the projective standard deviation where the variables are as defined in the text.
Figure 4B:
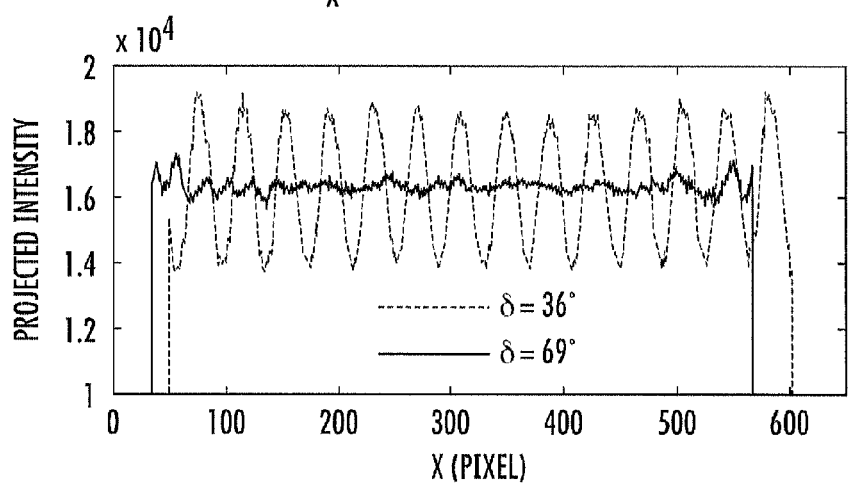
FIG. 4B illustrates projected line profiles of $A^\delta(p)$ for δ=−36° and δ=69° from the first image of the Si ⟨110⟩ RevSTEM dataset.

We overcome these challenges by measuring the lattice vector angles directly from real-space image intensities, referred to herein as the projective standard deviation (PSD). From a conceptual standpoint, the PSD calculates the standard deviation of STEM image intensities projected onto a series of vectors that emanate from a fixed point, e.g. the scan origin without loss of generality. As shown schematically in FIG. 4A the STEM image, $I(i,j)$, and dimensions, M×N, is projected onto a line $A^\delta$ with slope $\tan(\delta)$. The angle $\delta$ ranges from −90° to 90° with respect to slow scan direction $\vec{X}$. All pixels in $I(i,j)$ that fall within a projected range of $[p, p+1]$ on $A^\delta$ are then averaged. This is shown in FIG. 4A, where the shaded pixels are averaged as they are all projected within the indicated range. The projected average intensity, $A^\delta(p)$, is then:

$$A^\delta(p) = \begin{cases} \dfrac{\sum_{p \le P(i,j,\delta) < p+1} I(i,j)}{N(p,\delta)} & \text{when } N(p,\delta) \ge l_0 \\ 0 & \text{when } N(p,\delta) < l_0 \end{cases} \quad (6)$$

where $P(i,j,\delta)$ is the projected position of data point $(i,j)$ on line $A^\delta$ and $N(p,\delta)$ is the number of data points in the projected range $[p, p+1]$. The parameter $l_0$ is a critical value under which the projected information is not statistically significant due to insufficient data points, thus $l_0$ depends on the spatial sampling rate. Generally, $l_0^2$ must be slightly larger than the total number of pixels in a unit cell, Using the first frame of the ⟨110⟩ Si RevSTEM dataset, FIG. 4B shows a plot of $A^\delta(p)$ for $\delta=-36°$ and $\delta=69°$ with $l_0=100$. The line profile for $\delta=-36°$ shows periodic feature because $A^{-36°}$ is perpendicular to the crystallographic direction [1$\bar{1}$1] and thus produces a periodic intensity. Because $A^{69°}$ is not perpendicular to any low order directions, the projection averages out any periodic information. Taking the standard deviation of $A^\delta(p)$, i.e. the projective standard deviation, thus yields a metric of atom column periodicity perpendicular to a particular $\delta$, e.g. the PSD($\delta=-36°$) is much larger than PSD($\delta=69°$).

Figure 4C:
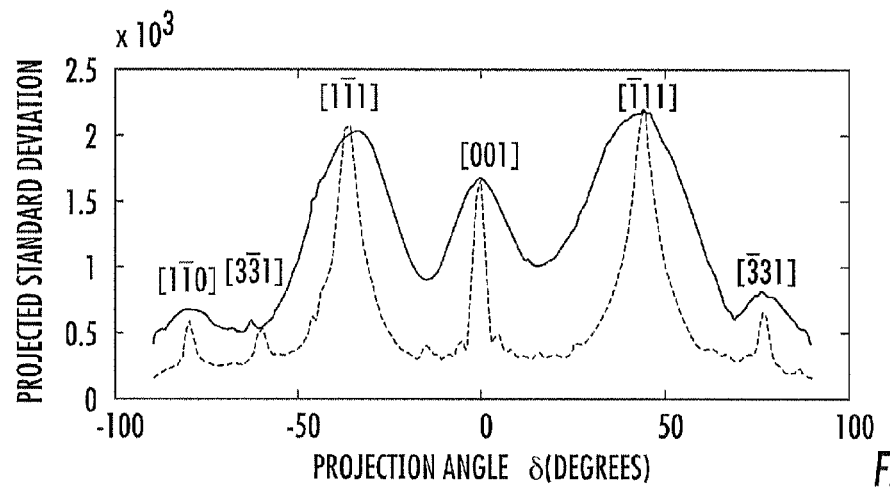
FIG. 4C illustrates PSD(δ) as a function of δ calculated using two different sized image areas: 465×465 (solid line) and 100×100 (dashed line) pixels.

The method provides a reliable and robust, measurement of crystallographic angles, even in the presence of noise, from small areas of an image (only requires >1 unit cells), and with significant drift distortion. Again using the ⟨110⟩ Si dataset, FIG. 4C shows the PSD($\delta$) for −90°≤$\delta$≤90° determined using a sub-area of the image. The two largest peaks are from Si [1$\bar{1}$1] and [$\bar{1}$11] directions, along which the atoms are more densely arranged. The peak at ~0° represents the [100] direction and the peak at −79° is from the [1$\bar{1}$0] direction. The other two small peaks at −60° and 78° correspond to [3$\bar{3}$1] and [$\bar{3}$31]. It is important to note that this data is from a single sub-area of noisy image and that all the peaks are sharp and well defined. While the step size for $\delta$ is 1°, the angle measurement precision is ±0.02° after fitting the peaks to Gaussian distributions. Moreover, by reducing the sub-area used to calculate the PSD to 100×100 pixels containing only about 1.5 unit cells, the method can be greatly accelerated. While the peaks broaden with reducing sub-area size as shown in the figure, they still exhibit well defined maxima and can be calculated in ~0.2 s with our unoptimized MATLAB script.

Figure 5:
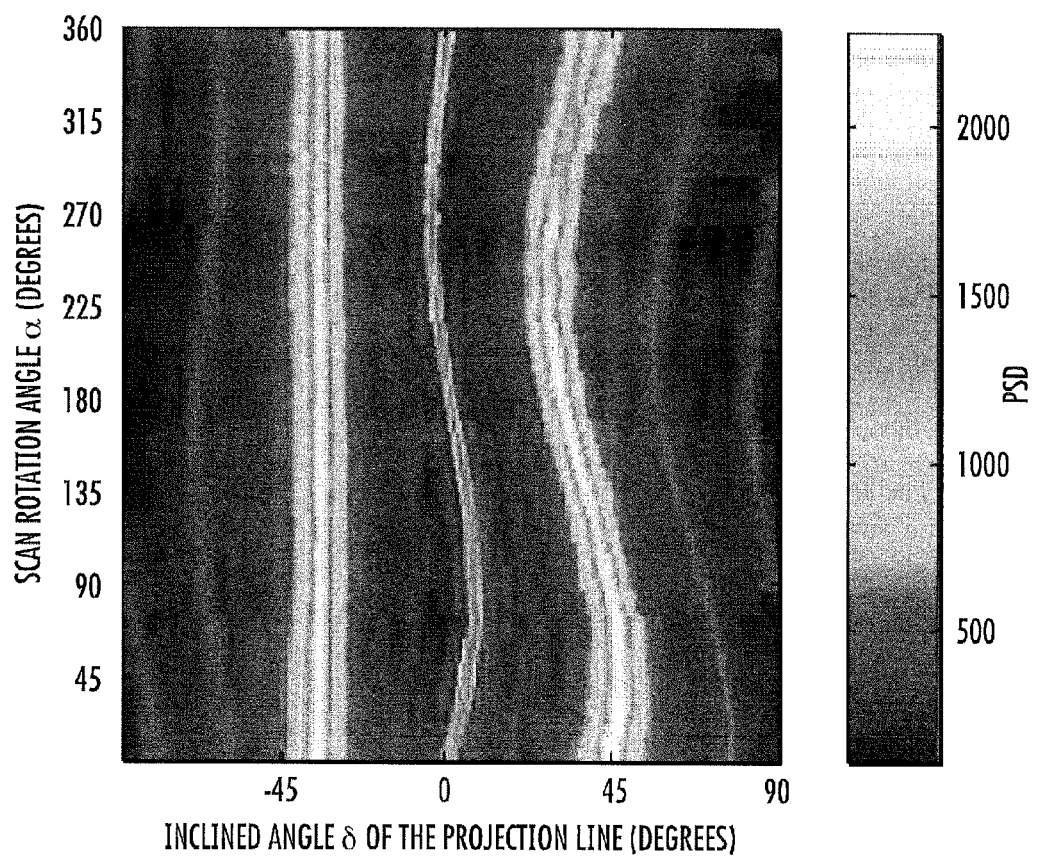
FIG. 5 is a diagram illustrating the projective standard deviation as a function of projection angle δ and scan rotation angle α across the entire 60 frame Si ⟨110⟩ RevSTEM dataset.

The PSDs calculated for all 60 frames in the Si image series are presented in FIG. 5. Due to the modulation of image distortion during scan rotation, e.g. FIG. 3B, the lattice vector angles corresponding to each $A^\delta$ peak are distorted along sinusoidal curves with the exception of ~$A^{-36°}$. As the sinusoidal amplitude correlates with observed distortion, the drift direction is approximately along [1$\bar{1}$1] and preserves this angle during scan rotation. We will return to this behavior after we consider how the lattice vector angles can be applied to measure the drift rate and direction.

3.2. Drift Vector Quantification

Up to this point, we have demonstrated that RevSTEM modulates the image distortion due to drift and that the PSD can be used to, measure the apparent lattice vector angles, $\beta(\alpha)$, at each scan rotation. The objective then is to use this information to determine the corresponding undistorted, ideal lattice vector angles, $\beta$. To quantify drift, we start by evaluating the change of the ith lattice vector angle ($\beta_i(\alpha)=90+\delta_i$) during transformation of the coordination system from $\mathbb{R}_{0\,0}$ to $\mathbb{R}_{0\,\alpha}$. Note that in the $\mathbb{R}_{0\,\alpha}$ coordination system with rotation angle $\alpha$, the lattice vector angles are transformed to $\beta_i(\alpha)+\alpha$. Without loss of generality we introduce a $\vec{v}_1=(\cos\beta_i, \sin\beta_i)'$ of unit length in $\mathbb{R}_{0\,0}$. From Eq. 4, $[T_\alpha]$ distorts according to:

$$[T_\alpha]\vec{v} = \begin{pmatrix} \dfrac{1}{1 - D(t)\cos(\theta + \alpha)} & 0 \\ \dfrac{D(t)\sin(\theta + \alpha)}{1 - D(t)\cos(\theta + \alpha)} & 1 \end{pmatrix} \begin{pmatrix} \cos(\beta_i + \alpha) \\ \sin(\beta_i + \alpha) \end{pmatrix} \quad (7)$$

$$= \begin{pmatrix} \dfrac{\cos(\beta_i + \alpha)}{1 - D(t)\cos(\theta + \alpha)} \\ \dfrac{D(t)\sin(\theta + \alpha)\cos(\beta_i + \alpha)}{1 - D(t)\cos(\theta + \alpha)} + \sin(\beta_i + \alpha) \end{pmatrix} \quad (8)$$

and thus, $$\beta_i(\alpha) = \tan^{-1}\left[\dfrac{D(t)\sin(\theta - \beta_i)}{\cos(\beta_i + \alpha)} + \tan(\beta_i + \alpha))\right] \quad (9)$$

with the angle of the distorted vector in coordination system $\mathbb{R}_0$ given by, $$\beta_i[\mathbb{R}_\alpha \to \mathbb{R}_0] = \beta_i(\alpha) - \alpha \quad (10)$$

By extracting at least one distorted lattice vector angles as function of α, and ensuring that there are more data points from image series than the number of fit parameters (D(t), θ, and ideal $β_i$'s), we have all the information needed to refine drift parameter, drift direction and the angles using standard optimization algorithms. Thus, when RevSTEM is combined with PSD, direct determination of the drift parameters becomes possible without the need for a-priori knowledge of the crystal structure. Moreover, when the drift direction is parallel to a lattice vector, i.e. $θ=β_i$ and $β_i[\mathbb{R}_{0β} \rightarrow \mathbb{R}_{00}]=β_i$ the observed angle will not change during scan rotation. As observed for the Si dataset presented in FIG. 5, visual inspection of the PSD(δ,α) plot provides an indication of the drift direction. With this theoretical framework in place, we next demonstrate the power of this approach to recover undistorted STEM images from two datasets corrupted by drift.

4. Application of RevSTEM 4.1. An Instructive Example

Figure 6:
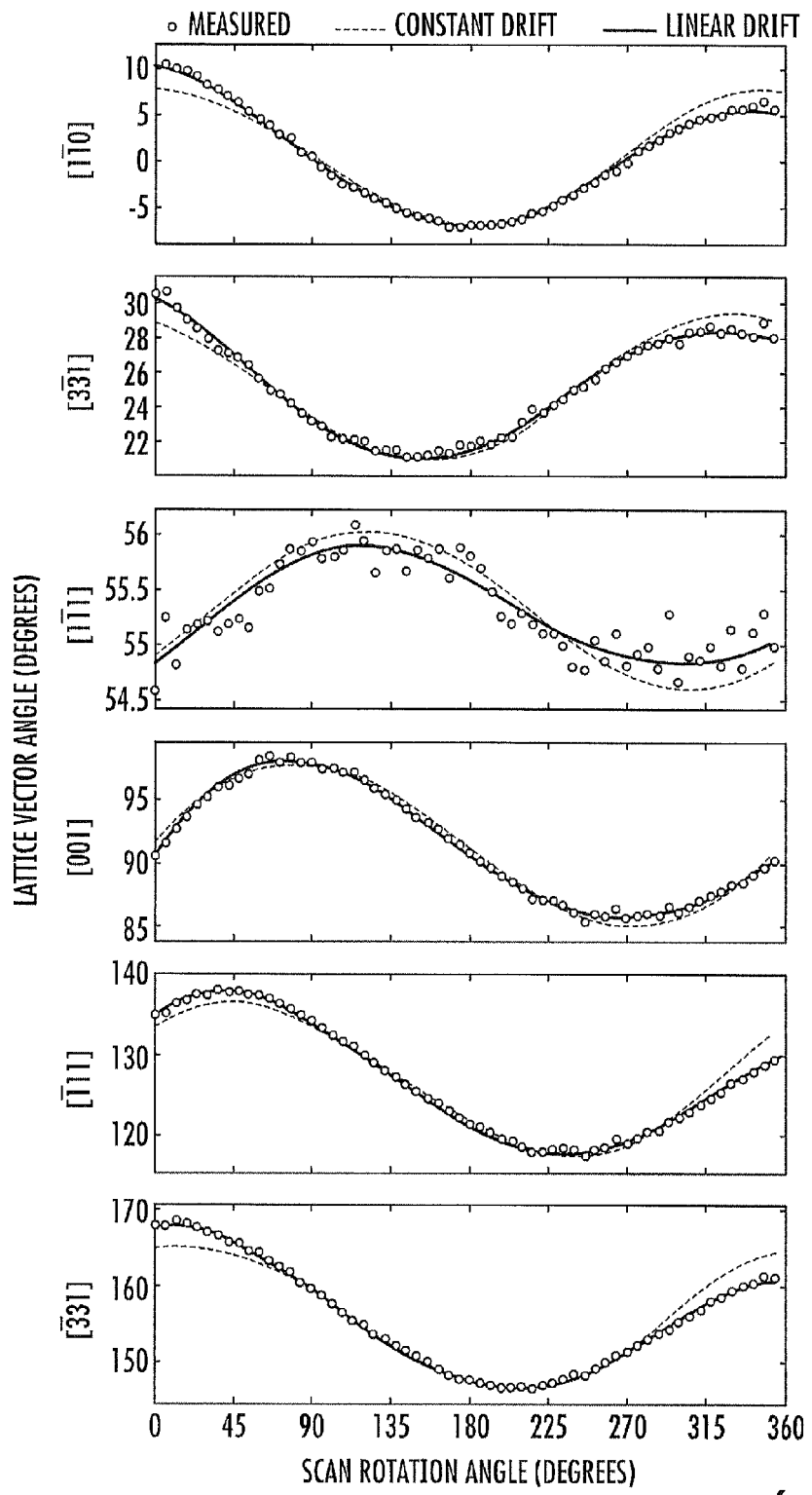
FIG. 6 includes graphs illustrating comparisons between measured lattice vector angles (filled circles) refined using two drift models, constant drift rate (red dashed lines) and linearly varying drift rate (solid lines), across the entire 60 frame Si ⟨110⟩ RevSTEM dataset.

We begin with an example using the Si dataset introduced in the previous section. While in the next section we show that the small 6° rotation step size for this dataset is unnecessary, the data provides a more visually instructive result. Moreover, as shown in FIG. 5, the excessive drift rate caused significant distortion to the image series as indicated by the lattice vector angle deviation of ~±10°. Thus, this dataset also provides an excellent test case to assess the performance of this method at high drift rates. With the traditional approach, these images could only be restored using a-priori information of the crystal structure. As discussed, RevSTEM provides all the information needed to obtain and correct for the drift parameter D(t) and θ. First, we extract the six lattice vector angles from FIG. 5 as a function α using the MATLAB peak finding algorithm (fmin), as shown in FIG. 6.

To determine the drift parameters, we apply a least-squares optimization process that minimizes a parameter R determined by:

$$R = \sum_\alpha \sum_i [β_{i,cal}(α)^2 - β_{i,exp}(α)^2] \quad (11)$$

where $β_{i,exp}$ and $β_{i,cal}(α)$ are the experimentally measured and calculated lattice vector angles from Eq. 9 respectively. Using this metric, the global minimum of R was searched using a Nelder-Mead simplex algorithm [25]. The initial values for $β_i$ are set as the average of $β_i(α)$ for all α, but are allowed to varying during the optimization. In practice, the initial values are not critical as the global minimum is well-defined. The optimization was performed using two models assuming: a constant drift rate and a linearly varying drift rate, D(t). Using the frame index u as a measure of time, the linearly-varying drift rate, D(u) is then defined as:

$$D(u)=D_0+D_1 u \quad (12)$$

where $D_0$ and $D_1$ are the relevant Taylor expansion coefficients.

Using the constant drift model, the refinement yields a drift parameter D=0.17 and θ=51.2°, with an R value of 340.48, The fitting results are shown in FIG. 6 where measured angles are indicated by filled circles and the calculated angles are indicated by dashed lines. Generally, the model matches the RevSTEM measurement, but with larger deviation at the beginning and the end of the series. These deviations suggest that a constant drift parameter introduces systematic error. Instead, optimization with a linear drift model estimates θ=51.9°, $D_0$=0.23, and $D_1$=−0.002 with R=31.45 at the global minimum. This indicates the drift parameter reduced from 0.23 to 0.11 across the series. A significant improvement of R can also be observed in FIG. 6 (solid lines) where excellent agreement is achieved across the entire RevSTEM series. The magnitude of the drift rate is particularly important as D≈0.2 corresponds to a drift rate of ~530 pm/s.

Once the drift parameters are refined, $[T_α]^{-1}$ can be calculated using Eq. 5 [26]. After applying the inverse distortion transformation and rotating from $\mathbb{R}_{0α}$ to $\mathbb{R}_{00}$ for each image in the series, we align all images using the usual cross-correlation approach with a precision of 1 pixel. All images in the series are then averaged together. These steps can introduce cropping of the image final image area. Primarily from the 6° increments, the final size of this dataset is 468×471 compared to the original 1024×1024 frames. As shown in the next section, however most of this cropping can be avoided by using a 90° rotation step size.

Compared with the first frame of the image series (FIG. 7A), the distortion corrected and averaged image in FIG. 7B exhibits negligible distortion or noise. Even more dramatic, FIGS. 7C and 7D show the three dimensional surface plots of sub-areas from FIGS. 7A and 7B. While it is nearly impossible to see the atom columns in the single frame, FIG. 7C, all atom column peaks are well-defined in the averaged image, FIG. 7D. Furthermore, each dumbbell pair in the RevSTEM image is clearly resolved.

Using the PSD method, the angle between [001] and [1$\bar{1}$0] in the corrected image was 90.3° and represents an error of only 0.3%. This value is a significant improvement over each frame where the distortion can be as large as ±10°. Moreover, this was achieved without prior structural knowledge and avoids the hazardous loop of assuming an observed structure and restoring back to the assumption. RevSTEM thus preserves the correct structure from distorted images without human interference. While the acquisition time for this Si dataset was 180 s for a 2π rotation, an increment step size of 90° also readily retrieves the lattice vector angles for drift parameter quantification as shown next.

4.2. A Practical Example

RevSTEM can be implemented using only a limited number of rotation angles, e.g. with an α step size of 90°. While in this case drift distortion is only captured along four directions, the optimization algorithm is still provided with sufficient data to determine D and θ. To demonstrate this capability, we acquired a 40 frame RevSTEM image series of $SrTiO_3$. For comparison, we acquired the first 20 frames of the series without scan rotation. The subsequent 20 frames were acquired with a rotation angle step size of 90°. For the rotating portion of the series, D and θ were refined using a constant drift model using measured lattice vector angles. In this case, a linear drift parameter does not significantly improve the fitting result.

Figure 8:
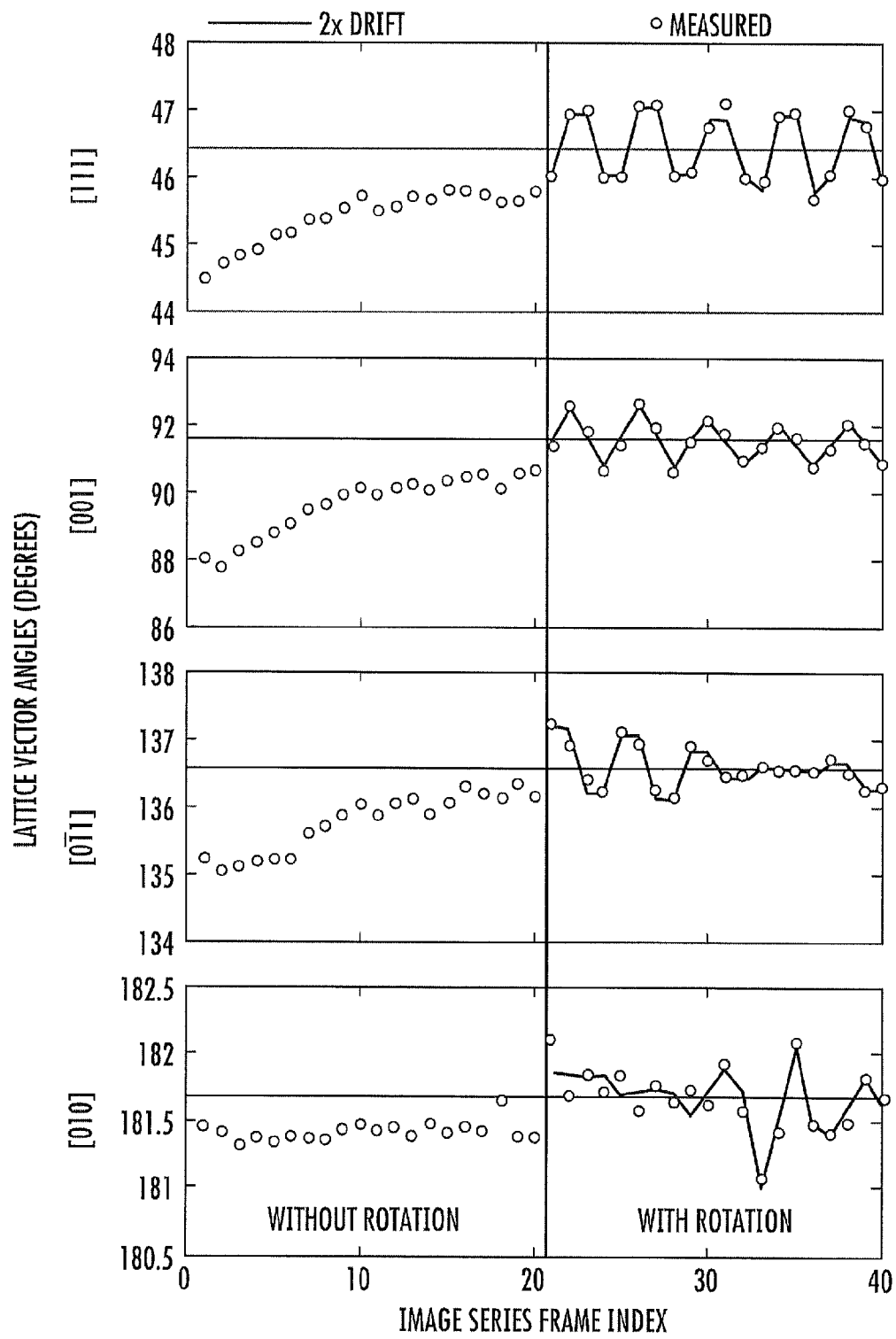
FIG. 8 includes graphs illustrating measured RevSTEM angles and linear drift model for $SrTiO_3$.

A comparison between the measured lattice vector angles [011], [001], [0$\bar{1}$1] and [010] with those from refinement are shown in FIG. 8 as a function of the frame index. For the first 20 frames without rotation, the lattice vector angles are consistent, but incorrect. This indicates a drift rate that decreases over time. Upon initiating scan rotation at frame 21, lattice vectors angles are seen to oscillate around the true value. From these data points, the refinement reported D=0.013, corresponding to a 59 pm/s drift rate, θ=77°.

Figure 9A:
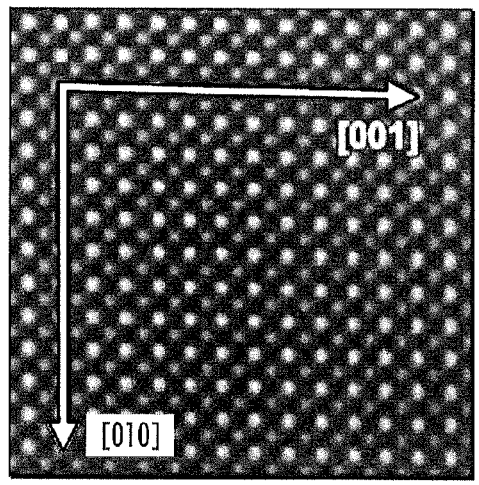
FIG. 9A is an image of the average of 20 frames of STEM images without rotation.
Figure 9B:
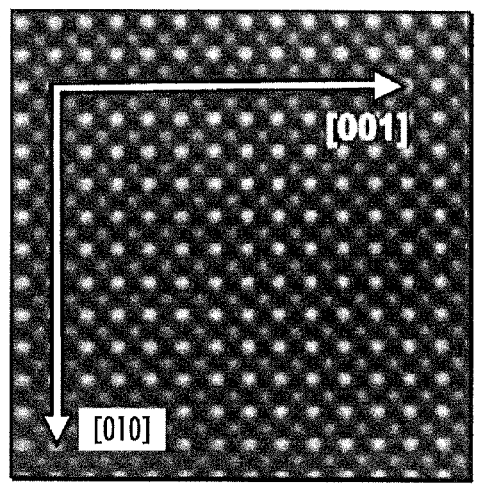
FIG. 9B is an image of the average of 20 frames of STEM images with rotation.

The result of averaging the first 20 frames without rotation, $I^{NR}$, is shown in FIG. 9A. The average of these frames cannot remove the distortion, which is then shared by all the frames. Using the PSD method, the angle between [100] and [010] in $I^{NR}$ is 91.8°. The angles for the last 20 frames start to oscillate around the true value. The RevSTEM average $I^R$ of these 20 frames with scan rotation is shown in FIG. 9B. In this case, the angle between [100] and [010] in $I^R$ is 90.11°, representing only 0.1% error. We have tested other image series and generally with RevSTEM method the angle is within ±0.1° of 90°. For cases of such small drift, a direct average of the rotation series can be applied but with atom column near edge experiencing a blur.

Figure 9C:
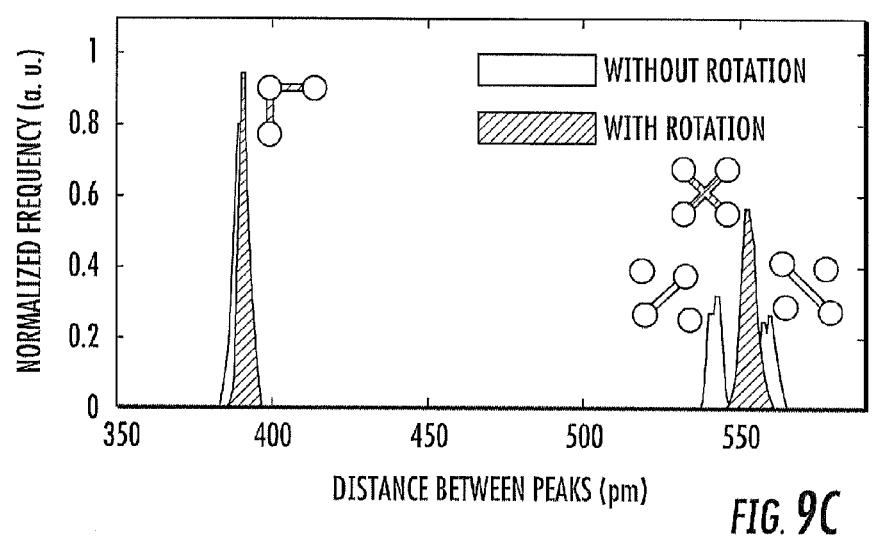
FIG. 9C is a distance histogram of ⟨100⟩ and ⟨110⟩ peaks calculated from the image data from FIGS. 9A and 9B.

With the excellent SNR, the atomic column positions can be located with vastly improved precision. Here, each atom column is located using a normalized cross-correlation approach and Gaussian peak fitting [16]. The centers of the Gaussian fittings are then used to calculate the distance between the atomic columns. Histograms of the peak distance corresponding to $\langle 100 \rangle$ and $\langle 110 \rangle$ lattice vectors are shown in FIG. 9C for $I^{NR}$ (unshaded area) and $I^R$ (shaded area) respectively. The $\langle 100 \rangle$ peak is from distance between Sr-Sr first like neighbor (FLN) and Ti-Ti FLN, while the $\langle 110 \rangle$ peak is from distance between Sr-Sr second like neighbor (SLN) and Ti-Ti SLN. Both images present a nice narrow peak for FLN. For the SLN peak, the RevSTEM shows one single peak while the simple image series shows two peaks, due to distortion of the image.

FLN and SLN peaks have been fit using Gaussian distribution for the RevSTEM. The pixel length was calibrated using the location of the FLN peak. The full width at half maximum (FWHM) for the two peaks are 3.6 pm and 5.8 pm, respectively. The σ for the peaks are calculated to be 1.5 pm and 2.5 pm, comparable with previous quantitative STEM work [22]. The ratio between the two distances is calculated to be 1.414, which agrees with $\sqrt{2}$.

In addition to preserving a larger final useful image area, the acquisition speed can be increased dramatically as only four frames are captured for a full rotation. One other advantage of the fast rotation over the slow rotation is that the fast rotation is more responsive to the change of drift rate and direction. The average can be calculated from the four frames and drift rate can be estimated from optimization. This opens up the possibility to predict the drift rate and shift the scan coordinates accordingly to make sure the area of interest is always in the view. Moreover, by controlling the total series acquisition time and probe current, the RevSTEM approach can also be applied to beam sensitive materials. Highly quantitative STEM work can be performed regardless of the sample drift rate and the distortion in the resulting RevSTEM images is always minimized.

5. Summary and Conclusion

Our results demonstrate that distortion-free STEM imaging can be achieved regardless of sample thermal stability. By introducing scan rotation between successive fast image frames and the PSD method track lattice vector angle distortion, we are able to characterize drift and remove its deleterious effects from each frame. Note that, while we have demonstrated HAADF drift correction, RevSTEM can be readily applied to any STEM imaging mode. The average of all the frames shows good SNR and much reduced distortion. The technique is applicable at both high and low drift rates, and independent of the size of the area of interest. Crucially, even large image areas can be acquired without the fear of drift distorting the available crystallographic information. As RevSTEM does not require a-priori structural information of the materials to calculate drift rate, analysis of unknown phases, defects, and interfaces becomes readily achievable in all directions, not just perpendicular to the scan direction.

While we have presented a RevSTEM acquisition routine that was developed for a FEI microscope, the approach is appropriate for any scan system that can introduce a rotation. Moreover, the approach should breath new life into previous generation STEM instruments with inherently less stable stages and thermal management. While we have focused our discussion on atomic resolution imaging of crystalline samples, the revolving imaging approach could be readily applied to the distortion correction at lower magnification and/or for a sample with aperiodic features with the development of appropriate feature tracking algorithms. With further development and integration RevSTEM imaging holds the potential to usher in a new era in quantitative analysis of atom columns in STEM.

Figure 10:
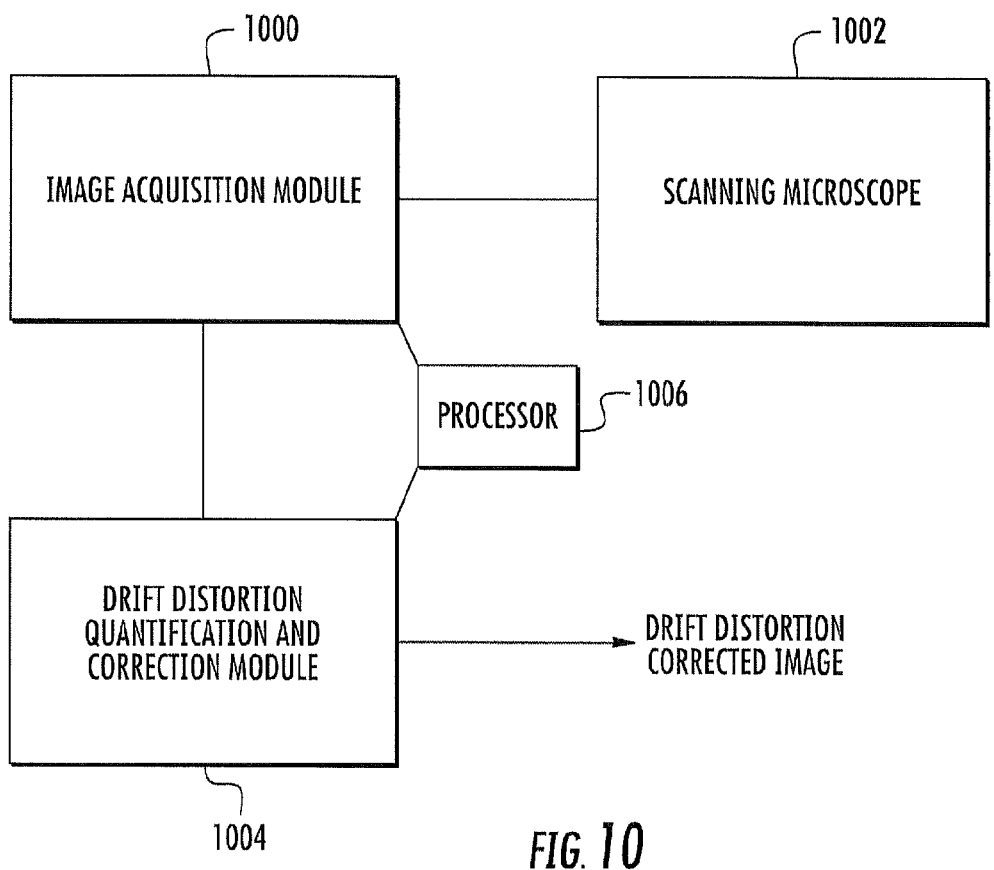
FIG. 10 is a block diagram illustrating an exemplary system for measuring and correcting sample drift distortion in a scanning microscopy system according to an embodiment of the subject matter described herein.

FIG. 10 is a block diagram illustrating an exemplary system for correcting sample drift distortion and scanning microscopy system according to an embodiment of the subject matter described herein. Referring to FIG. 10, an image acquisition module 1000 receives an image series acquired using a scanning microscope 1002 by rotating the scan coordinates of the microscope between image frames of the series. For example, the scan coordinates may be rotated by any suitable angle, such as 90 degrees, to obtain located images of the sample, as illustrated schematically above in FIGS. 3A and 3B. The system may further include a drift distortion quantification and correction module 1004 that determines at least one measurement of an angle or distance associated with an image feature as a function of the rotation angle from the series of rotated images. For example, drift distortion quantification and correction module 1004 may measure angles or distances associated with lattice vectors or other image features from the series of rotated images. Drift distortion quantification and correction module 1004 may use the measurements to determine a model for drift distortion in the series of images. For example, drift distortion quantification and correction module 1004 may assume a model for drift distortion and fit the model to the measured data points. The resulting model with model parameters determined by the fitting may be used to generate a drift distortion corrected image from the series of images. For example, an inverse drift distortion transformation may be applied to each of the rotated images. The rotated images may be rotated back to the original coordinate system. The images may be then mapped to each other and averaged to generate the drift distortion corrected image. The system may further include a processor 1006 on which modules 1000 and 1004 execute. Processor 1006 may be a component of scanning microscope 1002 or of a computing platform separate from scanning microscope 1002.

Figure 11:
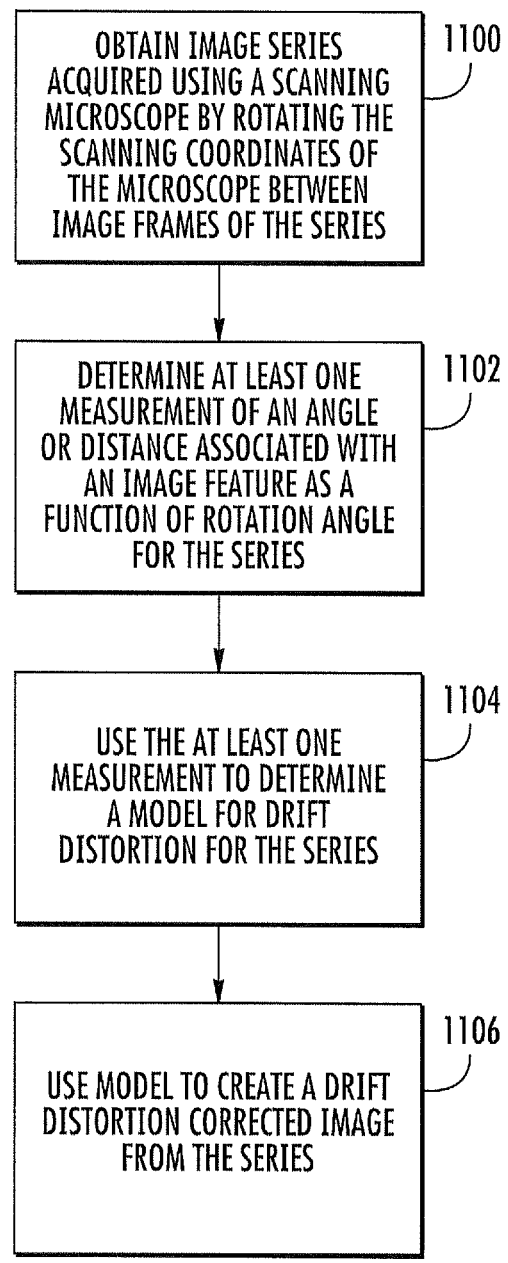
FIG. 11 is a flow chart illustrating an exemplary process for measuring and correcting sample drift distortion in a scanning microscopy system according to an embodiment of the subject matter described herein.

FIG. 11 is a flow chart illustrating an exemplary process for correcting sample drift distortion according to an embodiment of the subject matter described herein. Referring to FIG. 11, in step 1100, an image series is acquired using the scanning microscope by rotating scan coordinates of the microscope between successive image frames as obtained. For example, image acquisition module 1000 may obtain rotated images from scanning microscope 1002. In step 1102, at least one measurement of an angle or distance associated with an image feature as a function of rotation angle is determined from the series of rotated images. For example, module 1004 may measure at least one distorted lattice vector angle or distance. Alternatively, angles or distances associated with image features other than lattice vectors may be used. In step 1104, the measurements are used to determine a model for drift distortion in the series of images. For example, drift distortion quantification and correction module 1004 may use the one or more measurements of lattice vector angles and fit a model of drift distortion to the measurements. In step 1106, the drift distortion model is used to generate a drift corrected image from the series of images. An exemplary process for generating the drift corrected images is described above.

Because the methods and systems described herein are capable of generating drift corrected images, the resulting images can be used to quantify scan coil error caused by phenomena other than drift. For example, if the X and Y scan coils are not calibrated properly, because the subject matter described herein isotropically averages and eliminates drift distortion, the remaining distortion in the image may be due to scan coil error. This error can be quantified and eliminated.

Another feature of the subject matter described herein is to allow imaging at atomic resolution while drifting. For example, because drift can be corrected across different images, the sample may be allowed to drift while obtaining images and the resulting images can be combined without requiring the system to repeatedly image the same portion of the sample and thereby destroy the sample.

Although the examples described above relate to correcting drift distortion in a scanning transmission electron microscope, the subject matter described herein can be used to correct for drift distortion in images obtained using any suitable scanning microscope for which scan rotation is possible without departing from the scope of the subject matter described herein.

The disclosure of each of the following references is incorporated herein by reference in its entirety.

REFERENCES

[1] O. L. Krivanek, G. J. Corbin, N. Dellby, B. F. Elston, R. J. Keyse, M. F. Murfitt, C. S. Own, Z. S. Szilagyi, J. W. Woodruff, An electron microscope for the aberration-corrected era, Ultramicroscopy, 108 (2008) 179-195.

[2] R. F. Klie, C. Johnson, Y. Zhu, Atomic-Resolution STEM in the Aberration-Corrected JEOL JEM2200FS, Microsc, Microanal., 14(2008) 104-112.

[3] S. J. Pennycook, M. F. Chisholm, A. R. Lupini, M. Varela, A. Y. Borisevich, M. P. Oxley, W. D. Luo, K. van Benthem, S.-H. Oh, D. L. Sales, S. I. Molina, J. Garca-Barriocanal, C. Leon, J. Santamara, S. N. Rashkeev, S. T. Pantelides, Aberration-corrected scanning transmission electron microscopy: from atomic imaging and analysis to solving energy problems, Philosophical Transactions of the Royal Society A: Mathematical, Physical and Engineering Sciences, 367 (2009) 3709-3733.

[4] A. Y. Borisevich, H. J. Chang, M. Huijben, M. P. Oxley, S. Okamoto, M. K. Niranjan, J. D. Burton, E. Y. Tsymbal, Y. H. Chu, P. Yu, R. Ramesh, S. V. Kalinin, S. J. Pennycook, Suppression of Octahedral Tilts and Associated Changes in Electronic Properties at Epitaxial Oxide Heterostructure Interfaces, Phys. Rev. Lett., 105 (2010) 087204.

[5] A. Borisevich, O. S. Ovchinnikov, H. J. Chang, M. P. Oxley, P. Yu, J. Seidel, E. A. Eliseev, A. N. Morozovska, R. Ramesh, S. J. Pennycook, S. V. Kalinin, Mapping Octahedral Tilts and Polarization Across a Domain Wall in BiFe03 from Z-Contrast Scanning Transmission Electron Microscopy Image Atomic Column Shape Analysis, ACS Nano, 4 (2010) 6071-6079.

[6] C. T. Nelson, B. Winchester, Y. Zhang, S.-J. Kim, A. Melville, C. Adamo, C. M. Follunan, S.-H. Baek, C.-B. Eons, D. G. Schlom, L.-Q. Chen, X. Pan, Spontaneous Vortex Nanodomain Arrays at Ferroelectric Heterointerfaces, Nano Letters, 11(2011) 828-834.

[7] R. Aso, D. Kan, Y. Shimakawa, H. Kurata, Atomic level observation of octahedral distortions at the perovskite oxide heterointerface, Sci. Rep., 3 (2013).

[8] M. Saito, K. Kimoto, T. Nagai, S. Fukushima, D. Akahoshi, H. Kuwahara, Y. Matsui, K. Ishizuka, Local crystal structure analysis with 10-pm accuracy using scanning transmission electron microscopy, Journal of Electron Microscopy, 58 (2009) 131-136.

[9] K. Kimoto, T. Asaka, X. Yu, T. Nagai, Y. Matsui, K. Ishizuka, Local crystal structure analysis with several picometer precision using scanning transmission electron microscopy, Ultramicroscopy, 110 (2010) 778-782.

[10] F. He, C. L. Johnson, S. Lartigue-Korinek, G. Wang, P. R. Buseck, M. J. Htch, Calibration of projector lens distortions, Journal of Electron Microscopy, 54 (2005) 181-190.

[11] D. A. Muller, E. J. Kirkland, M. G. Thomas, J. L. Grazul, L. Fitting, M. Weyland, Room design for high-performance electron microscopy, Ultramicroscopy, 106 (2006) 1033-1040.

[12] B. Gipson, X. Zeng, Z. Y. Zhang, H. Stahlberg, 2dxUser-friendly image processing for 2D crystals, J Struct Biol, 157 (2007) 64-72.

[13] J. M. LeBeau, S. D. Findlay, L. J. Allen, S. Stemmer, Quantitative Atomic Resolution Scanning Transmission Electron Microscopy, Phys. Rev, Lett., 100 (2008) 206101.

[14] D. A. Muller, J. Grazul, Optimizing the environment for sub-0.2 nm scanning transmission electron microscopy, Journal of Electron Microscopy, 50 (2001) 219-226.

[15] H. S. von Harrach, Instrumental factors in high-resolution FEG STEM, Ultramicroscopy, 58 (1995) 1-5.

[16] J.-M. Zuo, A. B. Shah, H. Kim, Y. Meng, W. Gao, J.-L. Rouvire, Lattice and strain analysis of atomic resolution Z-contrast images based on template matching, Ultramicroscopy, 136 (2014) 50-60.

[17] P. D. Nellist, S. J. Pennycook, Accurate structure determination from image reconstruction in ADF STEM, J. Microsc., 190 (1998) 159-170.

[18] L. Jones, P. D. Nellist, Identifying and Correcting Scan Noise and Drift in the Scanning Transmission Electron Microscope, Microsc, Microanal., 19 (2013) 1050-1060.

[19] N. Braidy, Y. Le Bouar, S. Lazar, C. Ricolleau, Correcting scanning instabilities from images of periodic structures, Ultramicroscopy, 118 (2012) 67-76.

[20] M. J. Hytch, E. Snoeck, R. Kilaas, Quantitative measurement of displacement and strain fields from HREM micrographs, Ultramicroscopy, 74 (1998) 131-146.

[21] A. Renik, G. Mbus, S. Aturm, IMAGE-WARP: A real-space restoration method for high-resolution STEM images using quantitative HRTEM analysis, Ultramicroscopy, 103 (2005) 285-301.

[22] B. Berkels, R. Sharpley, P. Binev, A. Yankovich, F. Shi, P. Voyles, W. Dahmen, High Precision STEM Imaging by Non-Rigid Alignment and Averaging of a Series of Short Exposures, Microsc. Microanal., 18(2012) 300-301.

[23] P. Binev, F. Blanco-Silva, D. Blom, W. Dahmen, P. Lamby, R. Sharpley, and T. Vogt, Super-resolution image reconstruction by nonlocal means applied to high-angle annular darkfield scanning transmission electron microscopy (HAADF-STEM) in Modeling Nanoscale Imaging in Electron Microscopy (T. Vogt, W. Dahmen, P. Binev, eds.), Springer (2012), 127-145, Springer.

[24] J. P. Buban, Q. Ramasse, B. Gipson, N. D. Browning, H. Stahlberg, High-resolution low-dose scanning transmission electron microscopy, Journal of Electron Microscopy, 59 (2010) 103-112.

[25] Lagarias, J. C., J. A. Reeds, M. H. Wright, and P. E. Wright, Convergence Properties of the Nelder-Mead Simplex Method in Low Dimensions, SIAM Journal of Optimization 9 (1998) 112147.

[26] A. Klein, D. J. Kroon, Y. Hoogeveen, L. J. S. Kool, W. K. J. Renema, C. H. Slump, Multimodal image registration by edge attraction and regularization using a B-spline grid, SPIE, Lake Buena Vista, Fla., USA, 2011.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for measuring and correcting sample drift distortion in a scanning microscopy system, the method comprising:
   obtaining an image series of a sample acquired using a scanning microscope by rotating scan coordinates of the microscope between successive image frames;
   determining at least one measurement of an angle or distance associated with an image feature as a function of rotation angle from the series of rotated images;
   using the at least one measurement to determine a model for drift distortion in the series of images, wherein the sample comprises a crystal, the image feature comprises a lattice vector, and the measurements comprise distorted lattice vector angles; and
   using the drift distortion model to generate a drift corrected image from the series of images.

2. The method of claim 1 wherein determining at least one measurement includes determining the distorted lattice vector angles from real image space pixel intensities.

3. The method of claim 2 wherein determining the distorted lattice vector angles from real image space pixel intensities includes projecting pixel intensities from an image plane onto a line having a slope related to a projection angle of the line and determining a projected average pixel intensity for each point on the line.

4. The method of claim 3 wherein determining the distorted lattice vector angles from real image space pixel intensities includes determining a projective standard deviation comprising a standard deviation of the average pixel intensities projected onto the line.

5. The method of claim 4 wherein determining the distorted lattice vector angles includes determining projective standard deviations for a plurality of different projection angles to identify periodic features in the images and measuring the angles of the periodic features with respect to a fixed position.

6. The method of claim 1 wherein using the at least one measurement to determine a model for drift distortion in the series of images includes selecting a model for the drift distortion and fitting the model to the at least one measurement.

7. A method for measuring and correcting sample drift distortion in a scanning microscopy system, the method comprising:
   obtaining an image series of a sample acquired using a scanning microscope by rotating scan coordinates of the microscope between successive image frames;
   determining at least one measurement of an angle or distance associated with an image feature as a function of rotation angle from the series of rotated images;
   using the at least one measurement to determine a model for drift distortion in the series of images; and
   using the drift distortion model to generate a drift corrected image from the series of images, wherein using the drift distortion model to generate a drift corrected image includes applying an inverse distortion transformation based on the drift distortion model to each image in the series, rotating each image in the series to a common coordinate system, aligning the rotated images, and averaging the images.

8. The method of claim 1 comprising using the drift corrected image to quantify scan coil distortion.

9. The method of claim 1 wherein obtaining the series of images includes obtaining the series of images while drifting.

10. The method of claim 1 wherein the generation of the drift corrected image occurs without prior knowledge of structure of the sample.

11. A system for measuring and correcting a sample drift distortion and a scanning microscopy system, the system comprising:
    a processor;
    an image acquisition module executable by the processor for obtaining an image series of a sample acquired using a scanning microscope by rotating scan coordinates of the microscope between successive image frames; and
    a drift distortion quantification and correction module executable by the processor for determining at least one measurement of an angle or distance associated with an image feature as a function of rotation angle from the series of images and for using the measurements to determine drift distortion in the series of images, and for using the drift distortion model to generate a drift corrected image from the series of images, wherein the sample comprises a crystal, the image feature comprises a lattice vector, and the measurements comprise distorted lattice vector angles.

12. The system of claim 11 wherein determining at least one measurement includes determining the distorted lattice vector angles from real image space pixel intensities.

13. The system of claim 12 wherein determining the distorted lattice vector angles from real image space pixel intensities includes projecting pixel intensities from an image plane onto a line having a slope related to a projection angle of the line and determining a projected average pixel intensity for each point on the line.

14. The system of claim 13 wherein determining the distorted lattice vector angles from real image space pixel intensities includes determining a projective standard deviation comprising a standard deviation of the average pixel intensities projected onto the line.

15. The system of claim 14 wherein determining the distorted lattice vector angles includes determining projective standard deviations for a plurality of different projection angles to identify periodic features in the images and measuring the angles of the periodic features with respect to a fixed position.

16. The system of claim 11 wherein using the at least one measurement to determine a model for drift distortion in the series of images includes selecting a model for the drift distortion and fitting the model to the at least one measurement.

17. A system for measuring and correcting a sample drift distortion and a scanning microscopy system, the system comprising:
 a processor; and
 an image acquisition module executable by the processor for obtaining an image series of a sample acquired using a scanning microscope by rotating scan coordinates of the microscope between successive image frames; and a drift distortion quantification and correction module executable by the processor for determining at least one measurement of an angle or distance associated with an image feature as a function of rotation angle from the series of images and for using the measurements to determine drift distortion in the series of images, and for using the drift distortion model to generate a drift corrected image from the series of images, wherein using the drift distortion model to generate a drift corrected image includes applying an inverse distortion transformation based on the drift distortion model to each image in the series, rotating each image in the series to a common coordinate system, aligning the rotated images, and averaging the images.

18. The system of claim 11 comprising using the drift corrected image to quantify scan coil distortion.

19. The system of claim 11 wherein obtaining the series of images includes obtaining the series of images while drifting.

20. The system of claim 11 wherein the generation of the drift corrected image occurs without prior knowledge of structure of the sample.

21. A non-transitory computer readable medium comprising executable instructions that when executed by the processor of a computer control the computer to perform steps comprising:
 obtaining an image series of a sample acquired using a scanning microscope by rotating scan coordinates of the microscope between successive image frames;
 determining at least one measurement of an angle or distance associated with an image feature as a function of rotation angle from the series of rotated images, wherein the sample comprises a crystal, the image feature comprises a lattice vector, and the measurements comprise distorted lattice vector angles;
 using the at least one measurement to determine a model for drift distortion in the series of images; and
 using the drift distortion model to generate a drift corrected image from the series of images.

* * * * *